United States Patent
Perez et al.

(10) Patent No.: US 10,310,044 B2
(45) Date of Patent: Jun. 4, 2019

(54) METHOD OF CHARACTERIZING MOLECULAR DIFFUSION WITHIN A BODY FROM A SET OF DIFFUSION-WEIGHTED MAGNETIC RESONANCE SIGNALS AND APPARATUS FOR CARRYING OUT SUCH A METHOD

(71) Applicants: UNIVERSITE DE RENNES 1, Rennes (FR); CENTRE NATIONAL DE LA RECHERCHE SCIENTIFIQUE, Paris (FR); INSTITUT NATIONAL DE RECHERCHE EN INFORMATIQUE ET EN AUTOMATIQUE (INRIA), Le Chesnay (FR); INSTITUT NATIONAL DE LA SANTE ET DE LA RECHERCHE MEDICALE (INSERM), Paris (FR)

(72) Inventors: Patrick Perez, Rennes (FR); Olivier Commowick, Rennes (FR); Christian Barillot, Laille (FR); Aymeric Stamm, Montilly (FR)

(73) Assignees: UNIVERSITE DE RENNES 1, Rennes (FR); CENTRE NATIONAL DE LA RECHERCHE SCIENTIFIQUE, Paris (FR); INSTITUT NATIONAL DE RECHERCHE EN INFORMATIQUE ET EN AUTOMATIQUE (INRIA), Le Chesnay (FR); INSTITUT NATIONAL DE LA SANTE DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 15/104,218

(22) PCT Filed: Apr. 16, 2015

(86) PCT No.: PCT/EP2015/058250
§ 371 (c)(1),
(2) Date: Jun. 13, 2016

(87) PCT Pub. No.: WO2015/158811
PCT Pub. Date: Oct. 22, 2015

(65) Prior Publication Data
US 2017/0124294 A1   May 4, 2017

(30) Foreign Application Priority Data
Apr. 18, 2014 (EP) ..................... 14165298

(51) Int. Cl.
*G01R 33/563* (2006.01)
*G06F 19/00* (2018.01)
(Continued)

(52) U.S. Cl.
CPC ....... *G01R 33/56341* (2013.01); *G06F 17/18* (2013.01); *G06F 17/5009* (2013.01);
(Continued)

(58) Field of Classification Search
CPC .... G06F 19/702; G06F 17/18; G06F 17/5009; G06F 2217/16; G01R 33/56341
See application file for complete search history.

(56) References Cited

U.S. PATENT DOCUMENTS 9,632,161 B2 * 4/2017 Huwer ............ G01R 33/56341
2009/0010517 A1 * 1/2009 Basser ............ G01R 33/56341
382/131
(Continued)

FOREIGN PATENT DOCUMENTS

EP   2 458 397 A1   5/2012
WO   2014/052782 A1   4/2014

OTHER PUBLICATIONS

B. Jian et al., "A Unified Computational Framework for Deconvolution to Reconstruct Multiple Fibers From Diffusion Weighted MRI," IEEE Transactions on Medical Imaging, vol. 26, No. 11, Nov. 1, 2007, pp. 1464-1471, XP011195785.
(Continued)

*Primary Examiner* — Michael Jung
(74) *Attorney, Agent, or Firm* — Baker & Hostetler LLP

(57) ABSTRACT

A computer-implemented method of characterizing molecular diffusion within a body from a set of diffusion-weighted magnetic resonance signals by computing a weighted average of a plurality of multi-compartment diffusion models
(Continued)

comprises a same number of compartments, fitted to a set of diffusion-weighted magnetic resonance signals, the weighted average being computed using weights representative of a performance criterion of each of the models; wherein each of the multi-compartment diffusion models comprises a different number of subsets of compartments, the compartments of a same subset being identical to each other.

15 Claims, 5 Drawing Sheets

(51) Int. Cl.
 *G06F 17/18* (2006.01)
 *G06F 17/50* (2006.01)
 *A61B 5/055* (2006.01)
(52) U.S. Cl.
 CPC ............ *G06F 19/702* (2013.01); *A61B 5/055* (2013.01); *G06F 19/707* (2013.01); *G06F 2217/16* (2013.01)

(56) References Cited

U.S. PATENT DOCUMENTS

| | | | | |
|---|---|---|---|---|
| 2010/0004527 A1* | 1/2010 | Dale | ............... | G01R 33/56341 600/410 |
| 2010/0005427 A1* | 1/2010 | Zhang | ................... | G06F 3/011 715/863 |
| 2010/0106002 A1* | 4/2010 | Sugiyama | .............. | A61B 5/055 600/410 |
| 2012/0187946 A1* | 7/2012 | Stamm | ............. | G01R 33/56341 324/309 |
| 2012/0280686 A1* | 11/2012 | White | .............. | G01R 33/56341 324/309 |
| 2013/0004049 A1* | 1/2013 | Weeden | .................. | A61B 5/055 382/131 |
| 2013/0249555 A1* | 9/2013 | Chen | .................... | G01R 33/561 324/309 |
| 2013/0335080 A1* | 12/2013 | Jo | ........................ | G01R 33/561 324/309 |
| 2014/0091790 A1* | 4/2014 | Huwer | ............. | G01R 33/56341 324/307 |
| 2014/0136174 A1* | 5/2014 | Audigier | ............. | G06F 19/3481 703/11 |
| 2014/0294270 A1* | 10/2014 | Schneider | .............. | A61B 5/055 382/131 |
| 2014/0309520 A1* | 10/2014 | Lee | .................. | G01R 33/56366 600/419 |
| 2014/0357979 A1* | 12/2014 | Basser | ............... | G01R 33/5608 600/410 |
| 2015/0253410 A1* | 9/2015 | Warfield | ................ | A61B 5/055 324/309 |
| 2016/0018504 A1* | 1/2016 | Magin | .................... | A61B 5/055 324/309 |

OTHER PUBLICATIONS

T. Schultz et al., "Multi-Diffusion-Tensor Fitting via Spherical Deconvolution: A Unifying Framework," MICCAI 2010, Part 1, LNCS, vol. 6361, Sep. 2010, pp. 674-681, XP019151768.

Y. Paran et al., "Water Diffusion in the different microenvironments of breast cancer," NMR in Biomedicine, vol. 17, No. 4, Jun. 25, 2004, pp. 170-180, XP055125914.

E. Panagiotaki et al., "Compartment models of the diffusion MR signal in brain white matter: A taxonomy and comparison," Neuroimage, vol. 59, No. 3, Sep. 2011, pp. 2241-2254, XP028435369.

A. Stamm et al., "Fast Identification of Optimal Fascicle Configurations from Standard Clinical Diffusion MRI Using Akaike Information Criterion," IEEE International Symposium on Biomedical Imaging, China 2014.

D. Alexander et al., "Detection and Modeling of Non-Gaussian Apparent Diffusion Coefficient Profiles in Human Brain Data," Magnetic Resonance in Medicine, vol. 48, No. 2, pp. 331-340, 2002.

B. Scherrer et al., "Reliable Selection of the Number of Fascicles in Diffusion Images by Generalization Error," IPMI, 2013, vol. 7917, pp. 742-753.

C. Demiralp et al., "Generalizing Diffusion Tensor Model Using Probabilistic Inference in Markov Random Fields," MICCAI CDMRI Workshop, 2011.

T. Behrens et al., "Probabilistic diffusion tractography with multiple fibre orientations: What can we gain?" NeuroImage, vol. 34, No. 1, pp. 144-155, 2007.

D. Jones, "The effect of gradient sampling schemes on measures derived from diffusion tensor MRI: a Monte Carlo study," Magn. Reson. Med., vol. 51, No. 4, pp. 807-815, 2004.

D. Posada et al., "Model selection and model averaging in phylogenetics: Advantages of Akaike information criterion and Bayesian approaches over likelihood ratio tests," Syst. Biol., vol. 53, No. 5, pp. 793-808, 2004.

M. E. J. Newman, "Modularity and community structure in networks" PNAS Jun. 6, 2006 vol. 103, No. 23 pp. 8577-8582.

T. Peeters et al., "Analysis of Distance/Similarity Measures for Diffusion Tensor Imaging," Visualization and Processing of Tensor Fields, Advances and Perspectives XVII, Springer 2009.

M. Jenkinson et al., "FSL.," NeuroImage, vol. 62, No. 2, pp. 782-790, (2012).

N. Wiest-Daessle et al., "Rician noise removal by nonlocal means filtering for low signal-to-noise ratio MRI: Applications to DT-MRI," 11th International Conference on Medical Image Computing and Computer-Assisted Intervention, 2008, vol. 11.

A. MQuarrie et al., "The model selection criterion AICu," Statistics & Probability Letters 34 (1997) pp. 285-292.

B. Scherrer et al., "Parametric Representation of Multiple White Matter Fascicles from Cube and Sphere Diffusion MRI," PLOS ONE, vol. 7, Issue 11, Nov. 2012.

C. Poupon et al., "Regularization of Diffusion-Based Direction Maps for the Tracking of Brain White Matter Fascicles," NeuroImage 12, pp. 184-195 (2000).

B. Kreher et al., "Multitensor Approach for Analysis and Tracking of Complex Fiber Configurations," Magnetic Resonance in Medicine 54, 2005, pp. 1216-1225.

* cited by examiner

METHOD OF CHARACTERIZING MOLECULAR DIFFUSION WITHIN A BODY FROM A SET OF DIFFUSION-WEIGHTED MAGNETIC RESONANCE SIGNALS AND APPARATUS FOR CARRYING OUT SUCH A METHOD

CROSS-REFERENCE TO RELATED APPLICATIONS

This application is a National Stage of International patent application PCT/EP2015/058250, filed on Apr. 16, 2015, which claims priority to foreign European patent application No. EP 14165298.2, filed on Apr. 18, 2014, the disclosures of which are incorporated by reference in their entirety.

FIELD OF THE INVENTION

The invention relates to a method of characterizing the random motion of water molecules due to thermal agitation within a body, hereafter referred to as the diffusion profile, from a set of diffusion-weighted magnetic resonance signals. The invention also relates to an apparatus for carrying out such a method.

The inventive method and apparatus apply in particular, albeit not exclusively, to tractography and to the study of the microstructure of white matter in the human or animal brain.

BACKGROUND

Diffusion-weighted magnetic resonance imaging (dMRI or DW-MRI) is a non-invasive imaging technique that provides an indirect measurement of the diffusion profile over a finite spatial grid of points called voxels (three-dimensional pixels). Assessment of the diffusion profile is particularly useful for the study of the white matter microstructure. Indeed, the white matter is partly constituted of axons that can be thought as cylindrically shaped cells with impermeable membranes. As such, water trapped within axons is subject to restricted diffusion mainly along the axons' axis. The axon-specific diffusion profile thus carries valuable information about the axon structure itself (e.g., orientation, diameter). However, the diffusion-weighted signal is measured at the scale of the voxel, the size of which—typically 2×2×2 $mm^3$—defines the spatial resolution of the diffusion-weighted images. Due to hardware limitations of the MRI scanner, a voxel cannot be made as small as the cells to be characterized, but instead contains thousands of axons with possibly different orientations and might also contain other types of white matter cells. A common approach to account for that is to mentally regroup axons into bundles with common orientation, hereafter referred to as fascicles, and to model the diffusion profile at the voxel level as a mixture of diffusion profiles in multiple fascicles. This type of modeling is hereafter referred to as multi-compartment model (MCM), where each compartment represents a fascicle. Other diffusion profiles might be added in the mixture to account for freely diffusing water (water not trapped within cells) or water trapped in glial cells. Therefore, assessment of the voxel-dependent diffusion profile as an MCM provides valuable information about the tissue architecture, which may be of scientific and/or clinical relevance. DW-MRI of the brain is also at the basis of tractography, which is a 3D-modeling technique used to virtually represent neural tracts.

DW-MRI provides a collection of diffusion-weighted (DW) images, each one of them being obtained by the application of a magnetic field spatial gradient, hereafter referred to as a diffusion-sensitizing gradient (DSG), wherein the intensity of each voxel is proportional to how far water molecules in this voxel moved along the DSG direction during a given diffusion time, which is another imaging parameter. Diffusion can be probed at different length scales by varying the intensity of the DSG, set through a third imaging parameter called the b-value. From a collection of DW images, it is then possible to infer an MCM in each voxel and subsequently assess the underlying white matter microstructure.

However, due to the low spatial resolution of dMRI, —e.g. 2×2×2 $mm^3$, as mentioned above—several fascicles often coexist within a single voxel of the white matter, hindering both tractography and the determination of white matter microstructure.

Multi-compartment model selection allows overcoming this difficulty.

The DW signal for a given DSG can be analytically related to the parameters of the MCM that describe the diffusion of water in the different fascicles, provided that the number of non-parallel fascicles ("compartments") in the voxel is known a priori. The parameters of the model represent e.g. the fascicle orientations and occupancies (i.e. the fraction of the voxel volume occupied by each fascicle). Optimal values for these parameters can be determined by fitting the model to a collection of measured DW signals corresponding to different DSGs. However, the number of compartments is not known in advance in practice; therefore, determining the fascicle configuration within each voxel becomes a model selection problem, wherein both the optimal number of compartments and the parameters defining said compartments have to be estimated.

So far, this model selection problem has been solved either by brute-force methods or using Bayesian frameworks.

In brute-force approaches, a set of nested candidate MCMs with increasing number of fascicles is fitted to the measured DW signals. The best MCM is then identified as the candidate model that "best" fits the signals, where the comparison usually relies on an F-test [1]. Since the more complex the model, the better the fit, the F-test often tends to favor MCMs that over-fit the signals because the same signals are used for estimation and to assess goodness of fit. To limit overfitting, the Bayesian information criterion has been introduced to penalize model complexity that increases with the number of fascicles [2]. Document EP 2 458 397 suggests using the Akaike Information Criterion (AIC) for performing MCM selection. More recently, generalization error has been proposed to choose the "optimal" MCM based on its ability to predict new signals [3], thus avoiding the overfitting issue. These approaches limit their search of the "optimal" MCM to a predefined candidate set. Therefore, they do not make optimal use of the available information.

Differently, Bayesian frameworks try to estimate the "best" MCM as the one that maximizes a posterior distribution on the models. They rely on a careful choice of a prior distribution for MCMs. For instance, [4] uses Markov random fields (MRF) while [5] resorts to Automatic Relevance Detection (ARD) in which non-informative priors are assigned to all the MCM parameters except the mixture weights that are assumed to be Beta-distributed. Such priors automatically prune an entire compartment if it is not supported by the signals. These methods simultaneously perform model estimation and selection. When translated to clinics, however, Bayesian methods have limitations. First of all, they are prohibitively computationally expensive. Moreover, clinical DW-MRI often includes a single DSG intensity ("b-value") and a set of 30 DSG directions [6]. With such small sample sizes, the posterior distribution strongly depends on the prior, making the Bayesian information updating potentially ineffective.

SUMMARY OF THE INVENTION

The invention aims at overcoming these limitations of the prior art. More precisely, it aims at providing a MCM-based method of characterizing molecular diffusion within a body (e.g. estimating a voxel-wise diffusion profile) from a set of diffusion-weighted magnetic resonance signals, making a better use of the available information than brute-force model selection methods while being more simple and more robust to small sample sizes than Bayesian approaches.

An idea lying at the basis of the present invention, allowing achieving such an aim, is to replace model selection with model averaging. Instead of simply selecting one MCM out of a candidate set and discarding the others, several MCMs contribute, according to the quality of their fittings, to the determination of an "averaged" model.

Model averaging is known by itself, see e.g. [7]. However, it is not straightforward to "average" MCMs with different numbers of compartments. Another idea at the basis of the present invention is to convert the nested MCMs of the candidate set into "extended" models, with a same (and larger) number of compartments, which are then averaged. The expression "nested model" is well-known in the field of statistics: a nested model is obtained by fixing or suppressing one or more parameters from a more complex model Optionally, the averaged "extended" model can be simplified by a posteriori clustering to determine an optimal number of compartments.

An object of the present invention is then a computer-implemented method of characterizing molecular diffusion within a body from a set of diffusion-weighted magnetic resonance signals by computing a weighted average of a plurality of multi-compartment diffusion models comprising a same number of compartments, fitted to a set of diffusion-weighted magnetic resonance signals, said weighted average being computed using weights representative of a performance criterion of each of said models; wherein each of said multi-compartment diffusion models comprises a different number of subsets of compartments, the compartments of a same subset being substantially identical to each other.

The term "body" should be constructed broadly. Albeit the invention applies preferentially to the imaging of living bodies, and more particularly to animal or human bodies, it is not limited to them.

A "performance criterion" is a parameter quantifying a "performance" whose nature depends on the specific application considered. In the context of the invention, a relevant performance of the models is in particular their aptitude to fit the diffusion-weighted magnetic-resonance signals.

Particular embodiments of such a method constitute the subject-matter of dependent claims.

Another object of the present invention is a diffusion-weighted magnetic resonance apparatus comprising: at least a magnet for generating a static magnetic field, called longitudinal magnetic field, uniform within a volume of interest; at least a magnetic field gradient generator, for generating magnetic field gradients along a plurality of directions within said volume of interest; at least a radio-frequency pulse generator for emitting radio-frequency pulses within said volume of interest; at least a radio-frequency receiver for acquiring magnetic-resonance signals emitted by a body inside said volume of interest; and at least a processor, programmed or configured for driving said or each said magnetic field gradient generator and radio-frequency pulse generator and for processing said magnetic-resonance signals; wherein said or each said processor is programmed or configured for carrying out such a method.

BRIEF DESCRIPTION OF THE DRAWINGS

Additional features and advantages of the present invention will become apparent from the subsequent description, taken in conjunction with the accompanying drawings, wherein.

DETAILED DESCRIPTION

Figure 1:
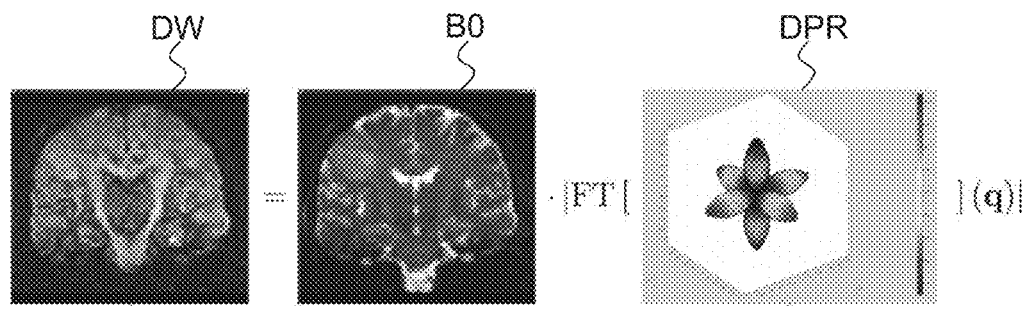
FIG. 1 illustrates the general principle of estimating the voxel-dependent diffusion profile of a body from DW signals.

As illustrated on FIG. 1, the general problem solved by the invention is to determine a voxel-dependent diffusion profile DPR from one or more diffusion-weighted images DW. It is known that DW-MRI provides a diffusion-weighted image DW that is related to DPR as follows:

$$DW = B0 \cdot |FT[DPR](q)| \quad (1)$$

where B0 is a "baseline image" (e.g. acquired by conventional, not diffusion-weighted MRI), FT is the Fourier transform operator and q the diffusion-sensitizing gradient. Directly inverting equation (1) to determine DPR from DW and B0 is impractical, as it requires a large amount of data and therefore very long scan times. For this reason, a multi-compartment model approach is a common approach.

Figure 2:
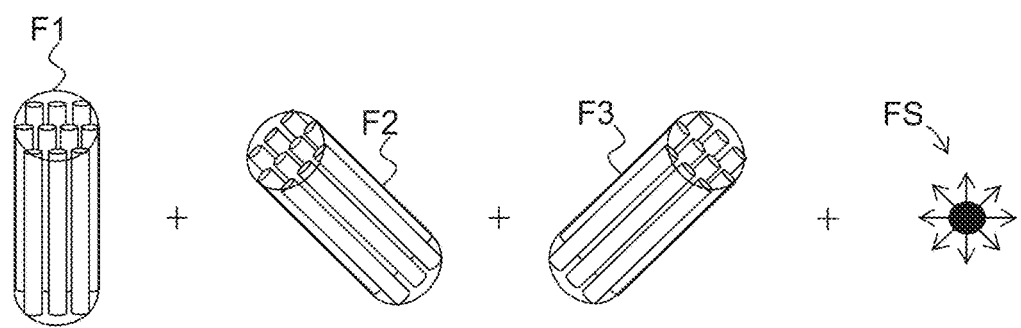
FIG. 2 is a very simplified representation of the white matter microstructure.

This approach is schematically illustrated by FIG. 2, which shows a very simplified representation of the microstructure of a small volume element (voxel) of the white matter of a human or animal brain. The voxel mainly contains three fascicles F1, F2 and F3, which constrain water diffusion, and "free space" FS, i.e. space outside the axons wherein water diffuses freely. The three "compartments" F1-F3 and FS occupy respective fractions $f_1$, $f_2$, $f_3$ and $f_0$ of the voxel volume ($f_0+f_1+f_2+f_3=1$). Each of them is characterized by a diffusion profile, $p_j^{fascicle}$ for fascicle Fj (j=1-3) and $p_0^{free}$ for free space. The resulting diffusion profile $p_x$ is then given by:

$$p_x = f_0 p_0^{free} + \sum_{j=1}^{M} f_j p_j^{fascicle} \quad (2)$$

where x is the three-dimensional position vector of the voxel and M is the number of fascicles (in the example of FIG. 2, M=3).

In the simplest model, called "ball and stick", it will be considered that diffusion is isotropic in free space and fully constrained along an orientation $\mu_j$—reflecting the axon orientation inside fascicles. Moreover, it is considered that all the diffusion profiles are expressed by a multivariate Gaussian distribution. Therefore:

$$p_0^{free} = \text{Gaussian}(0, d^{free} I_3) \quad (3a)$$

$$p_j^{fascicle} = \text{Gaussian}(0, d_j^{fascicle} I_3) \quad (3b)$$

where:

Gaussian (a,b) is a three-variate Gaussian distribution with mean "a" and variance "b" "a" being a three-element vector and "b" a 3×3 matrix;

0 is the [0 0 0] vector;

$I_3$ is the three-dimensional identity matrix;

$d^{free}$ is the diffusivity (proportional to the squared mean displacement) of water in free space;

$d_j^{fascicle}$ is the diffusivity of water in fascicle "j".

More complex models, such as "ball-and-zeppelin", "CHARMED" and "NODDI" are known in the art and can be applied to the present invention. For the sake of simplicity, however, only the "ball-and-stick" model will be considered, with the additional assumption $d^{free} = d_j^{fascicle} \forall j$.

According to the invention, a plurality of multi-compartment models, with an increasing number of parameters, are fitted to the DW signals. More particularly (although this is not essential), a "candidate set" consisting of (L+1) models identified by an index $l \in [0, L]$ will be considered. Even more particularly (although this is not essential), it will be considered that the l-th MCM comprises exactly l compartments, plus free space. Removal of these constraints is straightforward.

With these assumptions, it can be shown (see [5]) that the expected Diffusion-Weighted MRI signal $S_i(l)$ induced by a DSG with b-value b and direction $u_i$ has the following parametric form for $l \geq 1$ $$\frac{S_i^{(l)}}{S_0} = \left(1 - \sum_{j=1}^{l} f_j^{(l)}\right) e^{-bd^{(l)}} + \sum_{j=1}^{l} f_j^{(l)} e^{-bd^{(l)}(u_i^T \mu_j^{(l)})^2} \quad (4a)$$

where "$^T$" is the transposition operator, $S_0$ is the expected MR signal in absence of DSG and $\Theta_l = \{(\pm \mu_1^{(l)}, f_1^{(l)}), \ldots, (\pm \mu_l^{(l)}, f_l^{(l)}), d^{(l)}\}$ is the parameter set of the l-th "ball-and-stick" MCM where:

the fascicle orientations $\pm \mu_1^{(l)}, \ldots, \pm \mu_l^{(l)} \in \mathbb{S}^2$, $\mathbb{S}^2$ being the 2-sphere;

the fascicle occupancies; $f_1^{(l)}, \ldots, f_l^{(l)} \in [0,1]$;

the free diffusivity $d^{(l)} \geq 0$ varies across the models, but is the same for all the compartments of the model.

For $l = 0$ $$S_i^{(0)} = S_0 e^{-bd^{(0)}}$$

and $\Theta_0 = \{d^{(0)}\}$. $\quad (4b)$

For each model of the candidate set, the "optimal" parameter set $\Theta_l$ is determined by minimizing a suitable cost function, typically a quadratic error between the expected and the measured values of $S_i^{(l)}(b_i, u_i)/S_0$.

Then, a weighting coefficient is attributed to each MCM of the candidate set, fitted to the MR signals. For example, the weighting coefficient can be based on the Akaike Information Criterion (AIC) or a function thereof.

The AIC is an asymptotically unbiased estimator of the relative expected Kullbach-Leiber (KL) divergence between an estimated model and the true unknown model. It is defined as follows:

$$AIC = -2 \log \Lambda + 2K \quad (5)$$

where $\Lambda$ is the maximized value of the likelihood for the estimated model and K is the number of parameters of the estimated model. When the sample size N is small, the following "corrected" criterion, $AIC_c$, is recommended to avoid overfitting:

$$AIC_c = -2\log\Lambda + 2K + \frac{2K(K+1)}{N-K-1} \quad (6)$$

Since the true model is unknown, its AIC is approximated by the minimal AIC or $AIC_c$ among those of candidate models. Let $\{\mathcal{M}_l\}_{l=0,\ldots,L}$ be the set of candidate models. The AIC difference $$\Delta_l = AIC_c(l) - \min_{k \in [[0,L]]} AIC_c(k)$$

of model $\mathcal{M}_l$ can then be used to define its so-called Akaike weight $w_l$:

$$w_l = \frac{\exp\{-\Delta_l/2\}}{\sum_{k=0}^{L} \exp\{-\Delta_k/2\}} \quad (7)$$

The Akaike weight $w_l$ approximates the probability for $\mathcal{M}_l$ to be the best KL model. Such probabilities happen to be very useful. For instance, if the candidate models are sorted from largest to smallest Akaike weight, a 95% confidence set of models can be established by keeping the first p models such that $\Sigma_{l=0}^{p} w_l = 0.95$. An evidence ratio between models $\mathcal{M}_{l_1}$ and $\mathcal{M}_{l_2}$ can also be estimated as $w_{l_1}/w_{l_2}$ and used to assess how strongly $\mathcal{M}_{l_1}$ is more likely to be the best KL model compared to $\mathcal{M}_{l_2}$.

Weights can be computed based on different variants of the Akaike criterion known in the art, such as the unbiased Akaike Information Criterion $AIC_u$, which is particularly effective for preventing overfitting [12]. It is also possible to define weights based on completely different criteria expressing the MCM "goodness". For example, an information criterion measuring how well each model fits said diffusion-weighted magnetic resonance signals, e.g. the Bayesian Information Criterion (BIC) or the Hannan-Quinn Information Criterion (HQC) can be an advantageous choice when processing speed is important, e.g. in clinical applications. Conversely, generalization error is highly significant, as it reflects how well the model will predict new signals, but it leads to a very long computation time; it is then most suitable for research applications.

Whatever the criterion selected, the corresponding weight can be computed by a straightforward adaptation of equation (7).

According to the invention, the weights $w_l$ are used to compute model-averaged estimates of all the relevant parameters across all candidate models. In principle, the model-averaged estimate of a generic parameter $\theta$ is given by:

$$\hat{\theta} = \frac{\sum_{l=0}^{L} w_l 1_{\Theta_l}(\theta) \hat{\theta}_l}{\sum_{l=0}^{L} w_l 1_{\Theta_l}(\theta)}, \forall \theta \in \Theta_0 \cup \Theta_1 \cup \ldots \cup \Theta_L \quad (8)$$

where $1_{\Theta_l}$ is the characteristic function of the parameter set $\Theta_l$ of model $\mathcal{M}_l$ and $\hat{\theta}_l$ is the estimate of $\hat{\theta}_l$ under model $\mathcal{M}_l$.

However, application of equation (8) to a set of nested MCMs is not straightforward.

Indeed, for $l \in [[0,L]]$ only the parameter d appears in more than one MCM with the same interpretation as the free diffusivity (it actually appears in all of them). MCMs with an increasing number l of fascicles are nested and there is thus no pairwise matching of the fascicle compartments between two different MCMs, making model-averaged estimates of the fascicle orientations and occupancies hard to define. For example, when L=3, the unique fascicle of the 1-fascicle MCM "MCM1" can be averaged either with the first or with the second fascicle of the 2-fascicle "MCM2". Each of these two combinations can further be averaged with one of the 3 fascicles of the 3-fascicle "MCM3", leading to a total of 6 averaged fascicles.

In general, a candidate set made of MCMs from 0 to L fascicle compartments can generate up to L! fascicle combinations. To address this issue, the candidate MCMs are converted to "extended" models with a same fixed number L! of fascicle compartments, while ensuring a pairwise matching of the compartments between the MCMs. This is achieved by the indexing $$k = (m-1)\frac{L!}{(l-1)!} + (j-1)\frac{L!}{l!} + p \quad (9)$$

with $$p \in \left[1, \frac{L!}{l!}\right],$$

$m \in [1, (l-1)!]$ and $j \in [1,l]$, which yields the following reformulation of eq. (4a):

$$\frac{S_i^{(l)}}{S_0} = \left(1 - \sum_{k=1}^{L!} f_{L,k}^{(l)}\right) e^{-bd^{(l)}} + \sum_{k=1}^{L!} f_{L,k}^{(l)} e^{-bd^{(l)}(u_i^T \mu_{L,k}^{(l)})^2} \quad (10)$$

where $$f_{L,k}^{(l)} = \frac{l}{L!} f_j^{(l)} \text{ and } \mu_{L,k}^{(l)} = \mu_j^{(l)}.$$

Unlike equation (4a), equation (10) remains valid for l=0.

Finally, equation (8) can be applied to equation (10) to obtain model-averaged estimates of the ball-and-stick parameters as follows:

$$\hat{d} = \sum_{l=0}^{L} w_l \hat{d}^{(l)} \quad (11a)$$

$$\hat{f}_{L,k} = \sum_{l=0}^{L} w_l \hat{f}_{L,k}^{(l)} \quad (11b)$$

$$\hat{\mu}_{L,k} = E_1[D_{L,k}] \quad (11c)$$

with $$D_{L,k} = \frac{\sum_{l=0}^{L} w_l \hat{\mu}_{L,k}^{(l)} \hat{\mu}_{L,k}^{(l)\top}}{\sum_{l=1}^{L} w_l},$$

where $E_1[\bullet]$ is the principal eigenvector operator.

The obtained "averaged" MCM is then simplified by regrouping compartments that are representative of the same underlying fascicle structure. Any clustering algorithm that automatically detects the number of clusters and simultaneously performs the subsequent clustering can accomplish this task. One advantageous choice is to resort to a variant of the "modularity clustering" method, which is a graph-partitioning method originally proposed in the context of social sciences to detect strong communities within populations ([9]).

The original "modularity clustering" approach considers a graph, or network, comprising vertices interconnected by edges. It aims at determining whether there exists any natural division of its vertices into non-overlapping groups or communities, where these communities may be of any size.

The idea behind community clustering is that a "community structure" in a network corresponds to a "statistically surprising" arrangement of edges. The "surprising" character of the arrangement can be quantified by a measure known as modularity which is, up to a multiplicative constant, the number of edges falling within groups minus the expected number in an equivalent network with randomly placed edges.

More precisely, modularity $Q \in [0, 1]$ of a particular division of a n-vertex graph into two group is given by:

$$Q = \frac{1}{4m} s^T B s; \quad (12)$$

where:
s is a column vector whose elements $s_i$ are equal to 1 if vertex i belongs to group 1 and to −1 if it belongs to group 2;
B is a real symmetric matrix with elements $$B_{ij} = A_{ij} - \frac{k_i k_j}{2m} \quad (13)$$

with $A_{ij}$ is the number of edges between vertices i and j (element of the "adjacency matrix" A) and $m = \frac{1}{2} \Sigma_i k_i$ is the total number of edges in the networks, $k_i$ being the order of vertex i.

Bipartition of the graph is performed by maximizing Q. It can happen that the maximal achievable value of Q is zero, corresponding to a "trivial" partition wherein all the nodes belong to a same group. This is an acceptable result, meaning that the vertices form a single "community", no "natural" partition of which exists.

In order to subdivide a network into a number of groups greater than 2, one can proceed by repeated divisions into two, provided that each division increases the modularity. The additional contribution $\Delta Q$ to modularity upon further dividing a group g of size $n_g$ in two is:

$$\Delta Q = \frac{1}{2m} \left[ \frac{1}{2} \sum_{i,j \in g} B_{ij}(s_i s_j + 1) - \sum_{i,j \in g} B_{ij} \right] \quad (14)$$

The algorithm for performing modularity clustering is then:
(i) First of all, all the vertices of the graph are considered to belong to a same group;
(ii) A splitting of the group is attempted;
(iii) The modularity change $\Delta Q$ induced by the splitting is computed using eq. (14);
  a. If $\Delta Q > 0$, the splitting is validated; a further splitting of the groups thus obtained is attempted, starting from (i)
  b. If $\Delta Q \leq 0$, the splitting is not validated; the group is not subdivided further.
(iv) When all $\Delta Q$ are negative, the algorithm ends and the population is partitioned in K graphs such that the modularity is maximal.

Equations (12) to (14) are reproduced from [9] and do not apply directly to the problem of simplifying the averaged multi-compartment-model AVM. For that, the following preliminary operations are required:

First of all, the multi-compartment model is represented by a graph or network wherein each vertex corresponds to a fascicle compartment and each vertex is connected to all the other vertices through respective edges.

A "connectivity strength" value is associated to each edge, representing a "similarity value" between the compartments represented by the vertices interconnected by the edge.

The adjacency matrix A is redefined such that $A_{ij}$ is the connectivity strength between vertices i and j i.e. the similarity between compartments i and j. Similarly, $k_i$ is redefined as the sum of all the connectivity strength of the edges incident on vertex i and m as the sum of all the connectivity strengths.

Several choices of the "similarity value" between compartments are possible. For the determination of number of fascicles, orientation is the primary discriminative quantity. A suitable choice for this application is then the orientation similarity [9] that gives more strength to compartments sharing close principal orientations. A simple way to define an orientation similarity measure between two fascicles is to evaluate the squared scalar product between the orientations $\mu_i$, $\mu_j$ of the fascicle compartments: $S \propto (\mu_i \cdot \mu_j)^2$. Other similarity measures between fascicle compartments might be used instead, e.g. the "direction similarity" $S \propto (\mu_i \cdot \mu_j)$, whose square gives the orientation similarity. In particular, for MCMs that propose a higher level of description of the diffusion within fascicles by allowing 3-dimensional displacement of water molecules (not just along the fascicle orientation), a tensor representation ($D = d^{fascicle} \mu \mu^T + d_{perp1} e_{perp1} e_{perp1}^T + d_{perp2} e_{perp2} e_{perp2}^T$, where $e_{perp1}$ and $e_{perp2}$ are eigenvectors that span the space orthogonal to $\mu$ and $d_{perp1}$ and $d_{perp2}$ are the associated eigenvalues) of the compartments turns out to be useful and similarity measures between tensors can be used such as:

the "scalar product similarity" $S \propto \Sigma_{i,j} A_{ij} B_{ij}$, where $A_{ij}$ and $B_{ij}$ are the tensor representations of the two compartments whose similarity has to be determined (cf. [eq. 11 of [9]]);

the "tensor scalar product similarity": $S \propto \Sigma_{i,j} l_i^A l_j^B (e_i^A \cdot e_j^B)^2$ where $(l_i^A, e_i^A)$ is an eigenvalue/eigenvector pair for matrix A, and $(l_j^B, e_j^B)$ an eigenvalue/eigenvector pair for matrix B (cf. [eq. 12 of [9]]).

The clustering step described above is not essential. It is necessary to obtain an accurate representation of the microstructure of the body but it can be omitted in other applications, e.g. tractography.

Figure 3:
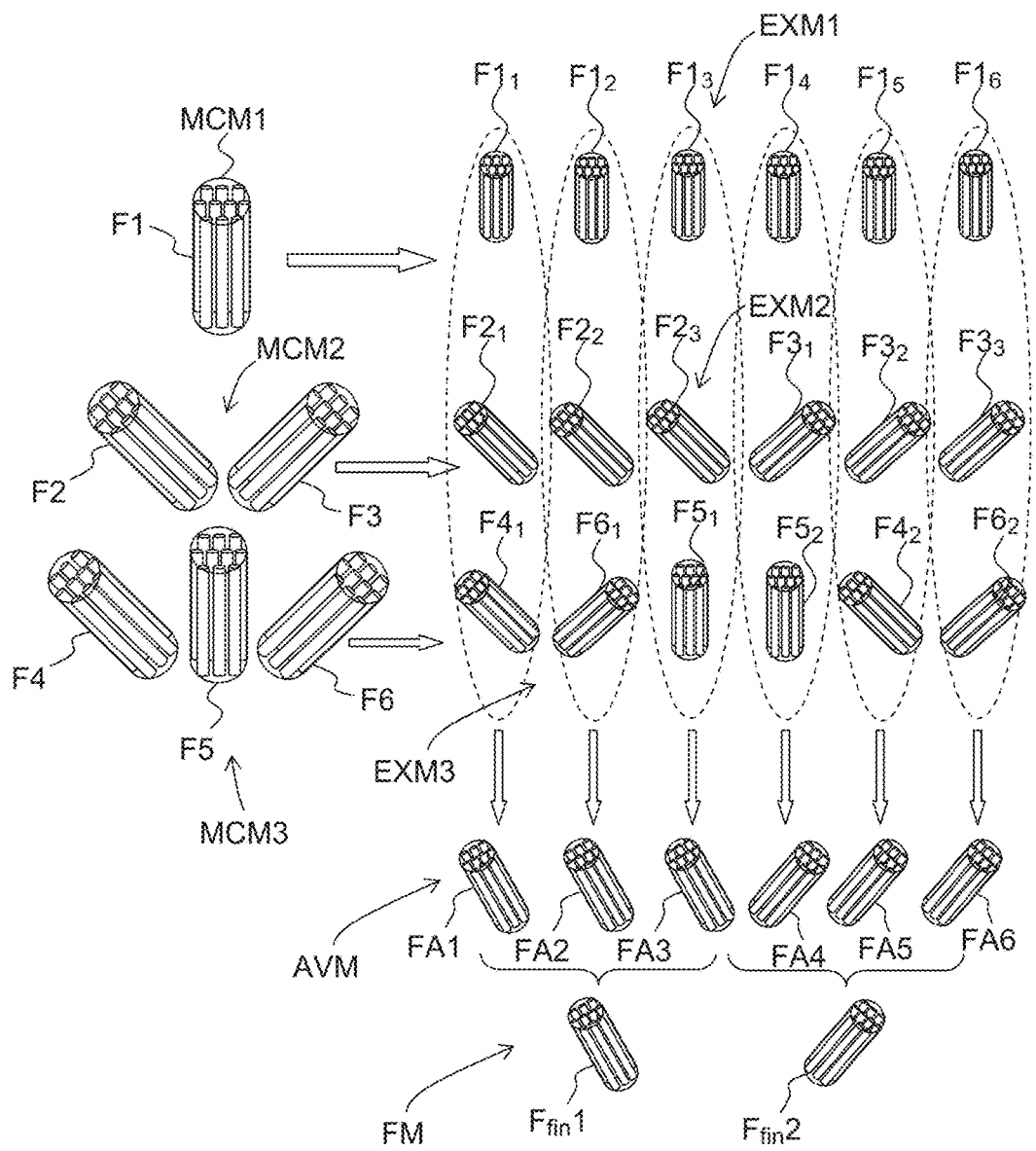
FIG. 3 illustrates an embodiment of the inventive method.

FIG. 3 illustrates schematically the whole method for the case L=3. Three multi-compartment models MCM1 (comprising a single compartment—i.e. fascicle—F1), MCM2 (comprising two compartments F2 and F3) and MCM (comprising three compartments F4, F5 and F6) are fitted to a set of DW signals corresponding to a single voxel of a human or animal brain, with different DSG directions. The orientations and proportion ("occupancy") of the compartments of each model are then determined so as to maximize the likelihood of the observed data under these models. In case of white Gaussian measurement noise, this corresponds to minimizing the quadratic difference between the observed signals and the signals predicted using the model. In general, a zero-compartment model only taking into account free diffusion is also used, but it is not represented on the figure for the sake of simplicity.

The multi-compartment models are then converted to respective 6-compartment (L!=6) extended models EXM1, EXM2 and EXM3.

Extended model EXM1 comprises six replicas $F1_1$-$F1_6$ of the single compartment of MCM1. Extended model EXM2 comprises three replicas $F2_1$-$F2_3$ and $F3_1$-$F3_3$ of each of the two compartments of MCM2. Extended model EXM3 comprises two replicas $F4_1$-$F4_2$, $F5_1$-$F5_2$ and $F6_1$-$F6_2$ of each of the three compartments of MCM3.

Homologous compartments of the different extended models are then averaged together, yielding a six-compartment (FA1-FA6) averaged model AVM.

In the example of FIG. 3, the voxel contains only two fascicles. As a consequence, the averaged model AVM can be partitioned into two sets of compartments, the compartments of each set being almost identical to each other. In particular, compartments FA1, FA2 and FA3 form a first set and compartments FA4, FA5 and FA6 a second set. A posteriori clustering of AVM provides then with final model FM comprising two compartments $F_{fin}1$ and $F_{fin}2$ approximating the diffusion properties of the two axon fascicles. Final models are obtained by averaging (preferably with weights provided by the clustering algorithm) compartments of AVM belonging to a same set.

An alternative approach, also comprised within the scope of the present invention, consist of directly fitting the extended models to the DW signals. Such an approach, however, is impractical because it makes the fitting much more complex and requires more data.

Figure 5:
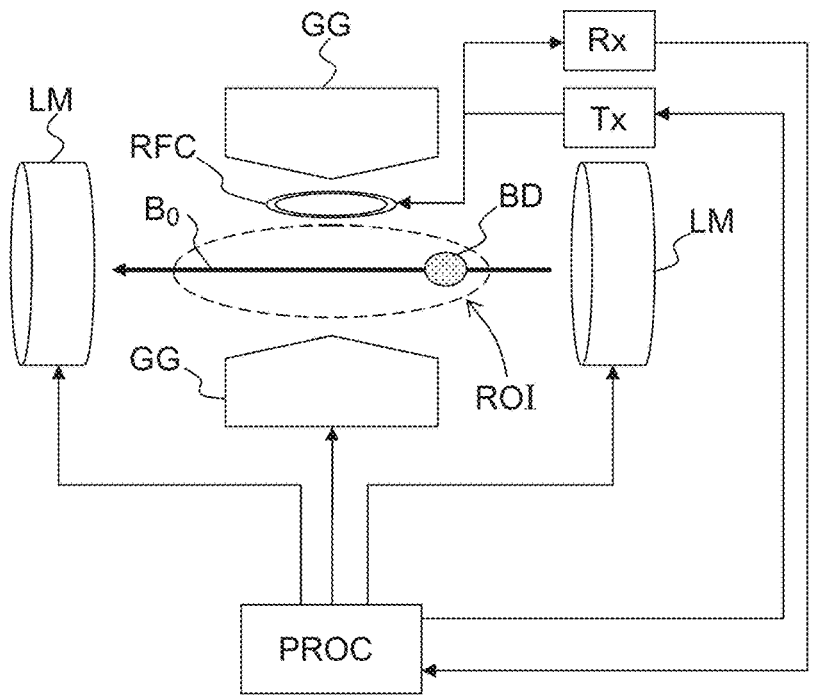
FIG. 5 is a simplified scheme of an apparatus according to an embodiment of the invention.

The inventive method can be carried out with the help of an apparatus of the kind illustrated on FIG. 5. The apparatus comprises a magnet LM for generating a longitudinal, stationary magnetic field $B_0$, substantially homogeneous within a region of interest ROI containing the body BD (e.g. a human or animal brain) whose diffusion properties are to be characterized; a set of magnets GG for generating magnetic field gradients—DSGs, but also spatial encoding and/or slice-selection gradients—within the ROI, and set of radio-frequency coils RFC connected to a radio-frequency pulse generator and emitter, Tx, and a MR signal receiver Rx. These elements form a MRI scanner, which may be conventional. Magnets LM and GG, and pulse generator Tx, are controlled by a processor PROC to perform DW-MRI as known in the art. The processor is also connected to receiver Rx to acquire and process DW signals according to the method described above. The term "processor" is to be constructed broadly; it can correspond to any data processing apparatus, comprising one or more computers and/or electronic circuits suitably programmed and/or configured.

The invented method has been tested by conducting a pilot study in which two healthy volunteers (S1 and S2) underwent a series of 10 DW-MRI scans on the same MR scanner (Siemens 3T Verio) with the same protocol. This protocol lasted 7 min and comprised a single non-weighted diffusion image B0 and 30 diffusion-weighted (DW) images acquired at b=1000 s/mm² along 30 non-collinear DSG directions u; uniformly spread over the north hemisphere. The following parameters were used: 128×128×60 image resolution with 2×2×2 mm³ voxels, TR=11 s and TE=99 ms.

Data were preprocessed with FSL [10], as follows:

(i) For each scan, (a) a rigid registration of the DW images on the B0 to correct for subject motion was performed and the gradient tables were rotated accordingly and (b) an affine registration of the DW images on the B0 was performed, guided by the previously estimated rigid transformation, to correct for distortions.

(ii) A rigid registration of the B0 images of the different scans on the B0 image of the first scan was performed, and the corresponding transformation was applied to the subsequent DW images. The gradient tables were rotated accordingly.

(iii) For each scan, the noise in the images was reduced using the Rician-adapted non-local means filter [11].

(iv) The brain was extracted using the BET algorithm.

(v) A WM mask was computed using the FAST algorithm.

According to known anatomy, the semioval center is an area where association, commissural and projection fascicles cross. As a consequence, it was necessary to fit MCMs up to at least 3 fascicles (L=3). One aim of the study was to show that setting L=3 yields a sufficient candidate set for model averaging. To this end, it was observed that the estimate of free water occupancy is highly biased for low L and gets better and stabilizes as L increases. Hence, the model averaging procedure was performed for L=3; 4 and the resulting free water occupancy maps were compared by means of Dice coefficient for different occupancy thresholds ranging in]0; 1[: if these two maps are highly similar, the contribution of the 4-fascicle MCM to the best MCM is negligible.

Another aim of the study was to compare the present approach to the ARD method as implemented in FSL [10] using L=3. ARD alters the estimation of the fascicle occupancies in such a fashion that $f_L^{ARD}$ estimates the probability that the L-fascicle MCM contributes to the best unknown MCM.

With the present approach, this probability is given by the Akaike ($AIC_c$) weight $w_L$ of the L-fascicle MCM. In order to compare $f_3^{ARD}$ and $w_3$, these indices were computed on 100 bootstrap DW images generated out of the original 10. For both indices, an FDR-corrected z-test of nullity was performed in all WM voxels. The aim was to compare the areas where the methods detect a statistically significant contribution of the 3-fascicle MCM to the best MCM, with respect to known anatomy. To this end, attention was focused on the semi-oval center and the mean of both indices were computed wherever significantly non null. It was also provided a qualitative visualization of the estimated fascicles.

To determine the maximal number of candidate MCMs, the Dice coefficient between binarized free water occupancy maps obtained with L=3; 4 was computed. Results are summarized in table 1.

TABLE 1

| $f_0$ Map Threshold | | 0.2 | 0.4 | 0.6 | 0.8 |
|---|---|---|---|---|---|
| Dice Score | S1 | 0.9987 | 0.9899 | 0.9818 | 0.9568 |
| | S2 | 0.9993 | 0.9940 | 0.9953 | 0.9957 |

For all thresholds employed, the Dice coefficient remained greater than 0.95, which means that including a 4-fascicle MCM in the averaging does not bring much additional information. It can the reasonably concluded that the contribution of the 4-fascicle MCM to the best MCM is negligible in the WM.

Figure 4A:
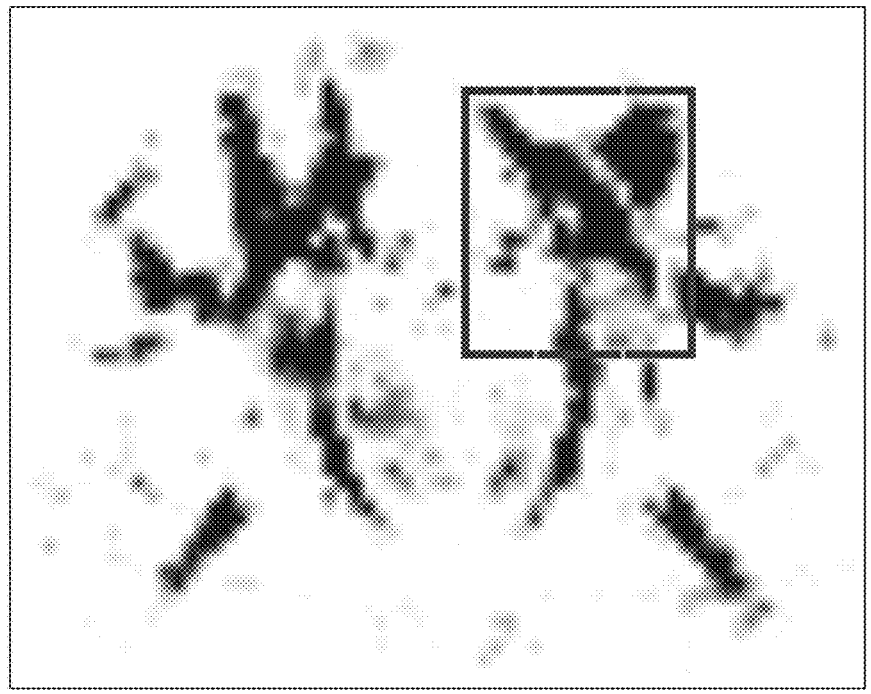
FIGS. 4*a*-4*d* illustrate a technical result of the invention.
Figure 4B:
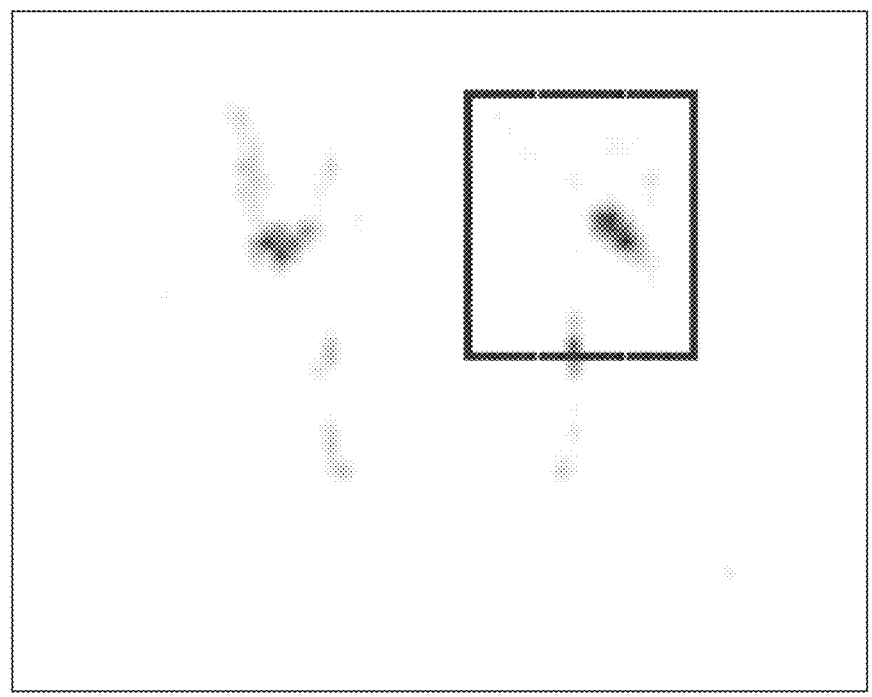
Figure 4C:
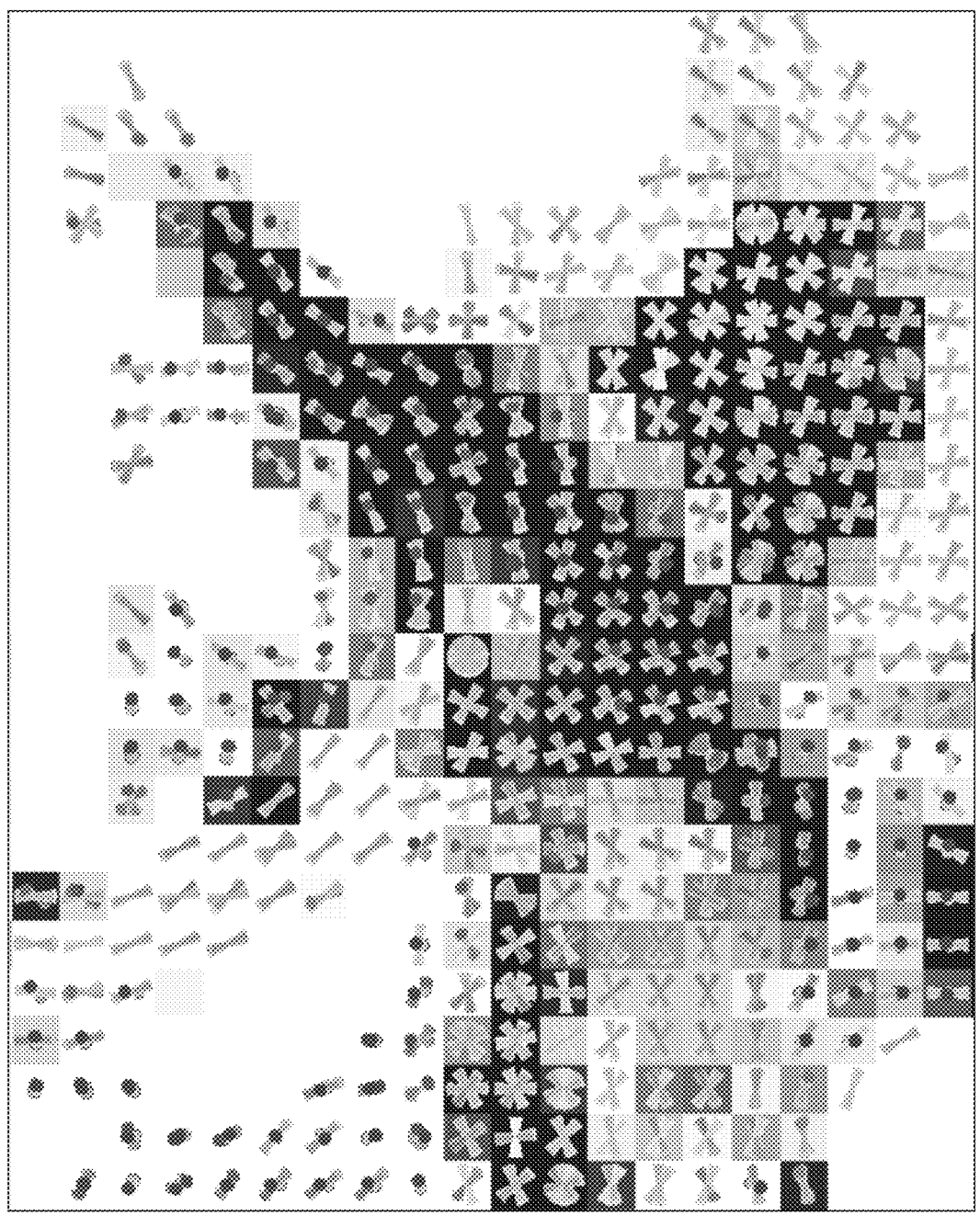
Figure 4D:
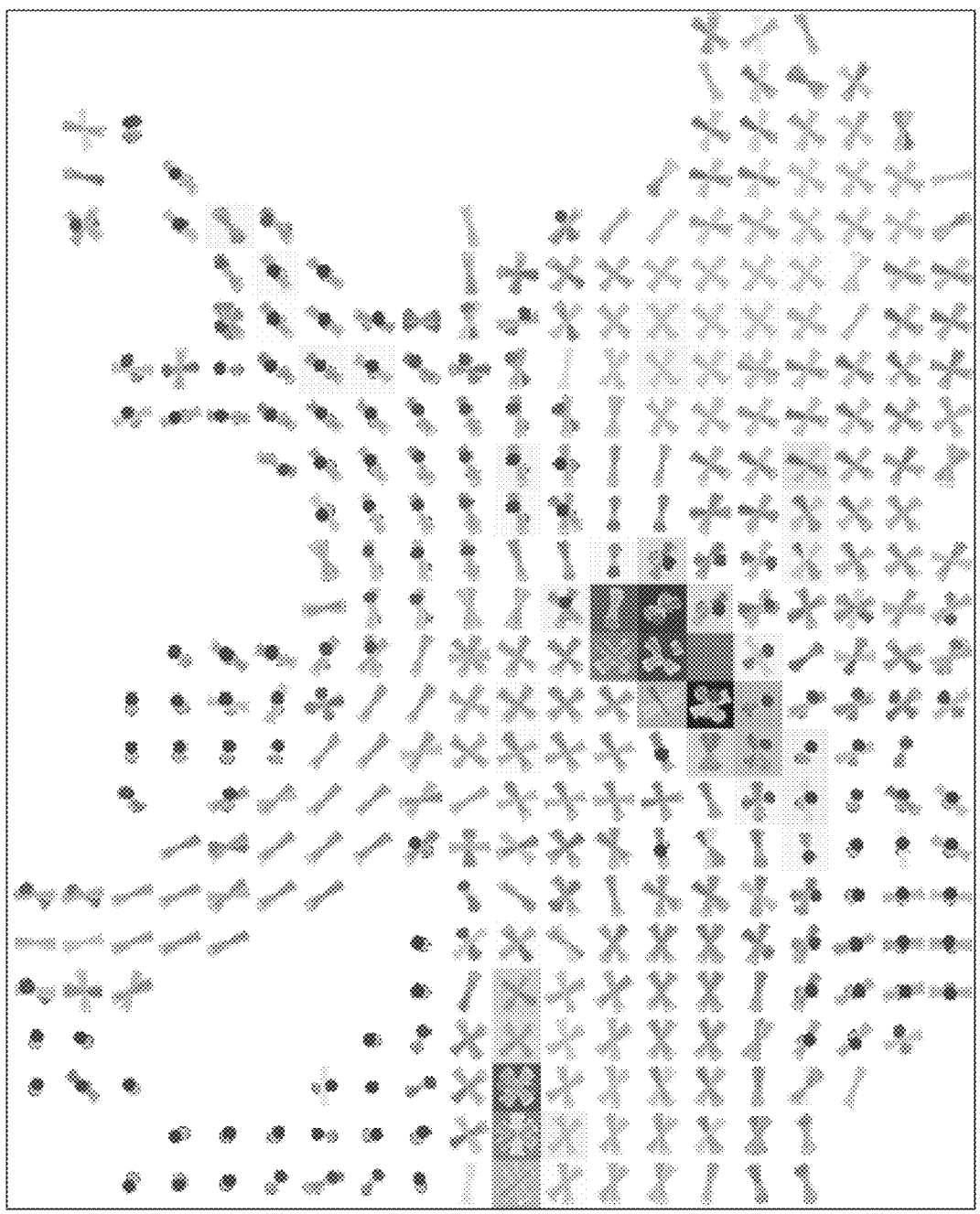

Comparison to ARD is illustrated by FIGS. 4a-4d. FIGS. 4a and 4b show, respectively, a global coronal view of the statistically significant mean probabilities $w_3$ and $f_3^{ARD}$ for volunteer S1 with a same window level. The comparison between these two features reveals that the present approach offers a more robust detection of statistically significant contributions of the 3-fascicle MCM to the best MCM. FIGS. 4c and 4d are zooms of FIGS. 4a and 4b, respectively, centered on the semi-oval center where it is expected to see predominantly 3 distinct fascicles. Results show that ARD (FIG. 4c) hardly identifies voxels with 3 fascicles. It also requires setting a threshold on the fascicle occupancies (here, 0.05) to discard fascicles with too low occupancy, on which the resulting fascicle configurations highly depend. In contrast, the present approach (FIG. 4d) does not need to set any parameters and, most of the time, correctly identifies 1 fascicle in the corpus callosum and 3 fascicles in the semi-oval center. Comparative performances were identical for S2. On FIGS. 4c and 4d the mean probabilities $w_3$ and $f_3^{ARD}$ are masked with the result of FDR-corrected z-test of nullity, and estimated fascicles are overlaid as equally shaped cones. Fascicle orientations are grayscale-coded and match the cone orientations.

The inventive method proved then to be more efficient than ARD in correctly identifying 3-fascicle crossing areas from data characterized by small sample size, suitable for clinical application. It is worth noting that no user-defined parameters are required contrary to ARD. From a computational point of view, the averaging procedure is very fast (a few seconds) but requires the estimation of MCMs up to 3 fascicles, which is a longer step. Nonetheless, estimation and averaging took about 5 hours for ARD and only 1 hour for the present approach on an 8-core computer, which makes it closer to a clinically acceptable running time.

The invention claimed is:

1. A diffusion-weighted magnetic resonance apparatus comprising:
   at least a magnet for generating a static magnetic field, called longitudinal magnetic field, uniform within a volume of interest;
   at least a magnetic field gradient generator, for generating magnetic field gradients along a plurality of directions within said volume of interest;
   at least a radio-frequency pulse generator for emitting radio-frequency pulses within said volume of interest;
   at least a radio-frequency receiver for acquiring magnetic-resonance signals emitted by a body inside said volume of interest;
   at least one processor;
   one or more computers and/or electronic circuits comprising the at least one processor; and
   a non-transitory computer-implemented program embodied on a computer readable medium configured to be executed on the at least one processor such that:

the at least one processor is configured for controlling said or each said magnetic field gradient generator, radio-frequency pulse generator and radio-frequency receiver and for processing said magnetic-resonance signals;

the at least one processor is configured to control said or each said magnetic field gradient generator, radio-frequency pulse generator and radio-frequency receiver to expose a body situated within said volume of interest to a magnetic resonance imaging process, wherein a plurality of magnetic gradients are applied to said body and, for each said magnetic gradient, acquiring a plurality of diffusion-weighted magnetic resonance signals for a plurality of voxels;

the at least one processor is configured to fit a plurality of nested multi-compartment diffusion models with an increasing number of compartments to said magnetic resonance signals, each said model being associated to a respective diffusion profile;

the at least one processor is configured to compute a weight, representative of a performance criterion, for each of said models;

the at least one processor is configured to convert said models into respective extended models having a same number of compartments by replicating each compartment of each model a predetermined number of times;

the at least one processor is configured to determine an averaged model by computing said weighted average of said extended models using the corresponding computed weights;

the at least one processor is configured to fit a plurality of nested multi-compartment diffusion models with an increasing number of compartments to said signals, each said model being associated to a respective diffusion profile;

the at least one processor is configured to compute a weight, representative of a performance criterion, for each of said models;

the at least one processor is configured to convert said models into respective extended models having a same number of compartments by replicating each compartment of each model a predetermined number of times;

the at least one processor is configured to determine an averaged model by computing said weighted average of said extended models using corresponding computed weights; and the at least one processor is configured to determine a voxel-dependent water diffusion profile within the biological tissue from the weighted average of a plurality of multi-compartment diffusion models.

2. A non-transitory computer-implemented program embodied on a computer readable medium configured to be executed on at least one processor to perform a method of characterizing water diffusion within biological tissue from a set of diffusion-weighted magnetic resonance signals, the method comprising:

a preliminary step of exposing a body to a magnetic resonance imaging process, wherein a plurality of magnetic gradients from at least a magnetic field gradient generator are applied to said body and, for each said magnetic gradient, a set of diffusion-weighted magnetic resonance signals is acquired for a plurality of voxels;

computing with at least one processor a weighted average of a plurality of multi-compartment diffusion models comprising a same number of compartments, fitted to the set of diffusion-weighted magnetic resonance signals, said weighted average being computed with the at least one processor using weights representative of a performance criterion of each of said models;

the method further comprising:

a) fitting with the at least one processor a plurality of nested multi-compartment diffusion models with an increasing number of compartments to said signals, each said model being associated to a respective diffusion profile;

b) computing with the at least one processor a weight, representative of a performance criterion, for each of said models;

c) converting with the at least one processor said models into respective extended models having a same number of compartments by replicating each compartment of each model a predetermined number of times; and d) determining with the at least one processor an averaged model by computing said weighted average of said extended models using the corresponding weights computed at step b), and determining with the at least one processor a voxel-dependent water diffusion profile within the biological tissue from the weighted average of a plurality of multi-compartment diffusion models, wherein each of said multi-compartment diffusion models comprises a different number of subsets of compartments.

3. The non-transitory computer-implemented program of claim 2, wherein said step a) comprises fitting L+1 nested multi-compartment diffusion models having $n_l$ compartments respectively, $l \in [0, L]$ being a model index, with $n_i < n_j$ for $i < j$.

4. The non-transitory computer-implemented program of claim 3 wherein, for each $l \in [0, L]$, $n_l = l$.

5. The non-transitory computer-implemented program of claim 4 wherein each said extended model has exactly L! compartments identified by labels $k \in [0, L!]$ given by:

$$k = (m-1)\frac{L!}{(l-1)!} + (j-1)\frac{L!}{l!} + p$$

with $$p \in \left[1, \frac{L!}{l!}\right],$$

$m \in [1, (l-1)!]$ and $j \in [1, l]$, all the compartments of a same extended model corresponding to a same pair (j,l) being replicas of a same compartment of the l-th multi-compartment diffusion model.

6. The non-transitory computer-implemented program of claim 2, wherein each said extended model has exactly N! compartments, wherein N is the maximum number of compartments of said nested multi-compartment diffusion models.

7. The non-transitory computer-implemented program of claim 2, wherein said step a) comprises fitting said nested multi-compartment diffusion models by maximizing the likelihood of said diffusion-weighted magnetic resonance signals under these models.

8. The non-transitory computer-implemented program of claim 2, wherein the weight computed at step b) are expressed as functions of estimators of Kullbach-Leiber divergences of said models.

9. The non-transitory computer-implemented program of claim 8, wherein said estimators of Kullbach-Leiber divergences of said models are chosen among: Akaike Information Criterion, AIC: Corrected Akaike Information Criterion, AICc; Unbiased Akaike Information Criterion, AICu.

10. The non-transitory computer-implemented program of claim 2, wherein the weights computed at step b) are expressed as functions of information criteria measuring how well each model fits said diffusion-weighted magnetic resonance signals.

11. The non-transitory computer-implemented program of claim 2, wherein the weights computed at step b) are expressed as functions of generalization errors.

12. The non-transitory computer-implemented program of claim 2, further comprising a step of:
   e) simplifying said averaged model by performing a posteriori clustering of its compartments.

13. The non-transitory computer-implemented program of claim 12, wherein said a posteriori clustering is performed by modularity clustering.

14. The non-transitory computer-implemented program of claim 12, wherein said clustering is performed based on a similarity measure between compartments, chosen among:
   an orientation similarity measure;
   a direction similarity measure;
   a scalar product similarity measure; and
   a tensor scalar product similarity measure.

15. The non-transitory computer-implemented program of claim 2, wherein said body is a part of a human or animal body.

* * * * *